(12) United States Patent
Weigand et al.

(10) Patent No.: US 8,987,477 B2
(45) Date of Patent: Mar. 24, 2015

(54) PHOTOCHROMIC BIS-IDENOFUSED NAPHTHOPRYANS

(71) Applicants: Udo Weigand, München (DE); Herbert Zinner, Rohrbach (DE); Yven Rohlfing, München (DE)

(72) Inventors: Udo Weigand, München (DE); Herbert Zinner, Rohrbach (DE); Yven Rohlfing, München (DE)

(73) Assignee: Rodenstock GmbH, Munich (DE)

( * ) Notice: Subject to any disclaimer, the term of this patent is extended or adjusted under 35 U.S.C. 154(b) by 0 days.

(21) Appl. No.: 14/363,410

(22) PCT Filed: Dec. 7, 2012

(86) PCT No.: PCT/EP2012/005067
§ 371 (c)(1),
(2) Date: Jun. 6, 2014

(87) PCT Pub. No.: WO2013/083282
PCT Pub. Date: Jun. 13, 2013

(65) Prior Publication Data
US 2014/0330028 A1 Nov. 6, 2014

(30) Foreign Application Priority Data
Dec. 9, 2011 (DE) .......................... 10 2011 120 645

(51) Int. Cl.
*C07D 311/94* (2006.01)
*C07D 311/96* (2006.01)
*G02B 5/23* (2006.01)
*G02B 1/04* (2006.01)

(52) U.S. Cl.
CPC ............ *C07D 311/96* (2013.01); *C07D 311/94* (2013.01); *G02B 5/23* (2013.01); *G02B 1/041* (2013.01)
USPC .......................................... 549/330; 549/381

(58) Field of Classification Search
CPC ............................ C07D 311/94; C07D 311/96
USPC ................................................... 549/330, 381
See application file for complete search history.

(56) References Cited

U.S. PATENT DOCUMENTS

| 5,645,767 A | 7/1997 | Van Gemert |
| 2012/0170098 A1 | 7/2012 | Takahashi |

FOREIGN PATENT DOCUMENTS

WO    2011/034202    3/2011

OTHER PUBLICATIONS

International Search Report and Written Opinion of the International Searching Authority, PCT/EP2012/005067, Mar. 6, 2013.

*Primary Examiner* — Taofiq A Solola
(74) *Attorney, Agent, or Firm* — McDonald Hopkins LLC

(57) ABSTRACT

The present invention relates to photochromic double-in-deno-fused naphthopyrans of the general formula (I) and the use thereof in plastics of all kinds, particularly for ophthalmic purposes. The photochromic compounds according to the invention are characterized by two distinct absorption bands of the open form in the visible wavelength range, i.e. two conventional photochromic dyes, each having only one discrete absorption band, can be replaced with dye molecules of this type. The compounds according to the invention, moreover, have a very good lifetime with a very high performance.

8 Claims, 2 Drawing Sheets

PHOTOCHROMIC BIS-IDENOFUSED NAPHTHOPRYANS

This application is a 35 U.S.C. 371 national stage filing and claims priority to PCT Application PCT/EP2012/005067 entitled "Photochromic Bis-Idenofused Naphthopryans," filed Dec. 7, 2012, which claims the benefit of German Application 10 2011 120 645.4 entitled "Photochromic Bis-Indenofused Naphthopyrans" filed Dec. 9, 2011, both of which are incorporated by reference herein in their entirety.

The present invention relates to photochromic double-indeno-fused naphthopyrans of the general formula (I) and the use thereof in plastics of all kinds, particularly for ophthalmic purposes. The photochromic compounds according to the invention are characterized by two distinct absorption bands of the open form in the visible wavelength range, i.e. two conventional photochromic dyes, each having only one discrete absorption band, can be replaced with dye molecules of this type. The compounds according to the invention, moreover, have a very good lifetime with a very high performance.

There has long been knowledge of various dye classes which, on irradiation with light of particular wavelengths, especially solar rays, reversibly change color. This is because these dye molecules are converted by light energy to an excited state, which they leave again in the event of interruption of the energy supply and revert to their starting state. These photochromic dyes include various pyran systems which have already been described in the prior art with different base systems and substituents.

Pyrans, specifically naphthopyrans and larger ring systems derived from these, are currently the class of photochromic compounds which has been the subject of the most work. Even though a patent was first filed as early as 1966 (U.S. Pat. No. 3,567,605), it was not until the 1990s that compounds which appeared suitable for use in spectacle lenses were developed. Suitable classes of pyran compounds are, for example, the 2,2-diaryl-2H-naphtho[1,2-b]pyrans or the 3,3-diaryl-3H-naphtho[2,1-b]pyrans, which, in excited form, exhibit various colors, such as yellow, orange or red-orange.

A further class of photochromic compounds of interest is that of more highly fused pyrans which absorb at a longer wavelength owing to their larger ring system and give red, violet and blue hues. These may be systems derived either from the 2H-naphtho[1,2-b]pyrans or the 3H-naphtho[2,1-b]pyrans, which originate from the particular naphthopyran systems by fusion on the f side.

2,2-Diaryl-2H-naphtho[1,2-b]pyrans with additional fusion on the pyrano-fused benzene ring are of great interest, since on account of their sizeable ring system they exhibit relatively long-wave absorption, allowing access to violet and/or blue darkening colors. The fusion relates to a substituted benzene ring (in the formula (I) of the compounds according to the invention that are described herein, accordingly, the benzene ring having the substituents $R_3$), which is further bridged in ortho-position with the naphthopyran.

If this bridging is produced only via one atom, the result is a five-membered ring fused onto the naphthopyran. The use of heteroatoms, particularly oxygen, as a bridge, is described in U.S. Pat. Nos. 5,651,923 and also 6,018,059. With carbon as bridging atom ("single-indeno-fused naphthopyrans"), a series of patent applications are in existence (e.g. EP 0 792 468, EP 0 906 366, EP 0 987 260, EP 1 054 010, EP 1 116 723 and EP 1 184 379), which differ primarily with regard to the two substituents on the bridging carbon atom. These substituents have a great influence on the lightening rate of the open (excited) form. The open forms of all of these photochromic dyes, which may additionally have other substituents such as alkyl or alkoxy on the non-indeno-fused benzene ring of the naphthopyran unit, each have no double absorption band in the visible wave-length range. Both EP 1 674 460 and WO 2011/034202 disclose single-indeno-fused naphthopyrans which additionally have an aryl substituent on the non-indeno-fused benzene ring of the naphthopyran unit. EP 0 912 908, EP 0 958 514, WO 2011/010744 and WO 2011/025056 disclose indeno-fused naphthopyrans which additionally also have a heterocyclic fusion on the non-indeno-fused benzene ring of the naphthopyran unit.

When this bridge is generated via two atoms, the result is a fused six-membered ring with various options solely for C, O and N. Compounds with C=O and N—R (lactam bridge) are described in U.S. Pat. No. 6,379,591. Compounds with an unsubstituted $CH_2$—$CH_2$ bridge and a fused heterocycle in the 7,8 position of the parent benzopyran are disclosed in U.S. Pat. No. 6,426,023. U.S. Pat. No. 6,506,538 describes the carbocyclic analog compounds in which the hydrogen atoms in the bridge may be replaced by OH, ($C_1$-$C_6$)-alkoxy, or two hydrogen atoms on one carbon atom may be replaced by =O. U.S. Pat. No. 6,022,495 describes, inter alia, compounds having a O—$CR^1R^2$ bridge. WO 2009/024271 describes analogous compounds having an additional fusion on the upper benzene ring.

When this bond is generated by three atoms, the result is a fused 7-membered ring with very many possible variations through insertion of heteroatoms. Compounds with a $CH_2$—$CH_2$—$CH_2$ bridge are described in U.S. Pat. No. 6,558,583. Here too, the hydrogen atoms in the bridge may be replaced by OH, ($C_1$-$C_6$)-alkyl or ($C_1$-$C_6$)-alkoxy, or two hydrogen atoms on one carbon atom may be replaced by =O. Given the same substitution pattern, they absorb at a shorter wavelength than the fused 6-membered rings.

US 2004/0094753 describes both compounds with a diatomic and with a triatomic bridge. The diatomic (carbon) bridge is additionally fused to a carbo- or a heterocycle. The triatomic bridge contains three carbon atoms or two carbon atoms and one oxygen atom with no additional fusion. Both rings may bear various substituents.

The different photochromic dyes available in the prior art, however, have disadvantages which, when used in sunglasses, significantly impair the wear comfort of the wearer. Firstly, the dyes have insufficiently long-wave absorption in the excited state and in the unexcited state. Secondly, there is frequently too high a thermal sensitivity of the darkening, and lightening may at the same time be too slow. Furthermore, the dyes available in the prior art often have an inadequate lifetime and hence allow only a short service life of the sunglasses. The latter becomes perceptible in rapidly declining performance and/or significant yellowing.

Common to the photochromic dyes in the prior art mentioned above is that they exhibit only one absorption band of the open form in the visible wavelength range. In order to achieve darkening phototropic glasses in neutral colors—i.e. in grey or brown hues—a balancing process between the different photochromic dyes of a mixture is required with respect to rate of lightening, lifetime and spectral excitation properties, so that the phototropic glass has the same hue at each time point of the darkening and lightening cycle. It would therefore be extremely valuable to be able to dispense with this balancing process.

Therefore, it is the object of the present invention to provide photochromic dyes which make it possible, in neutral colours—i.e. in grey or brown hues—to achieve darkening phototropic glasses with only one such photochromic dye. Such photochromic dyes, moreover, should be characterized by the combination of a long-wave absorption maximum of the closed form with a steep edge to the visible wavelength range, high darkening performance, very rapid lightening reaction and very good light stability.

This object is achieved by the subject matter indicated in the claims.

In particular, the photochromic double-indeno-fused naphthopyrans having the general formula (I) are provided:

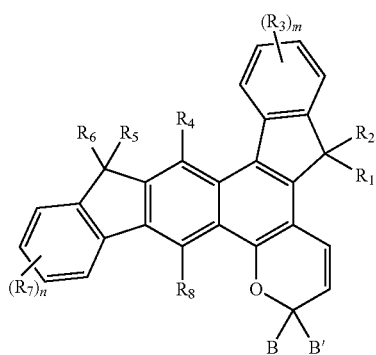

(I)

where the residues $R_1$, $R_2$, $R_3$, $R_4$, $R_5$, $R_6$, $R_7$ and $R_8$ are each independently a substituent selected from the group $\alpha$, consisting of a hydrogen atom, a ($C_1$-$C_6$)-alkyl residue, a ($C_1$-$C_6$)-thioalkyl residue, a ($C_3$-$C_7$)-cycloalkyl residue, which may have one or more heteroatoms selected from O or S, a ($C_1$-$C_6$)-alkoxy residue, a hydroxyl group, a trifluoromethyl group, bromine, chlorine, fluorine, an unsubstituted, monosubstituted or disubstituted phenyl, phenoxy, benzyl, benzyloxy, naphthyl or naphthoxy residue, in which the substituents may in turn be selected from the group $\alpha$, preferably from ($C_1$-$C_6$)-alkyl, ($C_1$-$C_6$)-alkoxy, bromine, chlorine or fluorine; m and n are each independently an integer from 1 to 4, or the residues $R_1$ and $R_2$, together with the carbon atom bonded to these residues, form a 5- to 7-membered carbocyclic or heterocyclic ring (i.e. heterocycles containing oxygen or sulfur atoms), which optionally carries one or more, preferably one to four, substituents from the group $\alpha$, it also being possible, however, for one to three aromatic or heteroaromatic ring systems to be fused onto this ring, the ring system or ring systems being selected independently of one another from the group $\beta$, consisting of benzene, naphthalene, phenanthrene, pyridine, quinoline, furan, thiophene, pyrrol, benzofuran, benzothiophene, indol and carbazol, which may in turn be substituted by one or more substituents selected from the group $\alpha$, and where, if two of these substituents borne by the 5- to 7-membered carbocyclic or heterocyclic ring are located on the same ring carbon atom, they may in turn form a 5- to 7-membered carbocyclic or heterocyclic ring, or the residues $R_5$ and $R_6$, together with the carbon atom bonded to these residues, form a 5- to 7-membered carbocyclic or heterocyclic ring (i.e. heterocycles containing oxygen or sulfur atoms), which optionally carries one or more, preferably one to four, substituents from the group $\alpha$, it also being possible, however, for one to three aromatic or heteroaromatic ring systems to be fused onto this ring, the ring system or ring systems being selected independently of one another from the group $\beta$, consisting of benzene, naphthalene, phenanthrene, pyridine, quinoline, furan, thiophene, pyrrol, benzofuran, benzothiophene, indol and carbazol, which may in turn be substituted by one or more substituents selected from the group $\alpha$, and where, if two of these substituents borne by the 5- to 7-membered carbocyclic or heterocyclic ring are located on the same ring carbon atom, they may in turn form a 5- to 7-membered carbocyclic or heterocyclic ring, or two adjacent residues $R_3$ form a fused-on benzene ring, which may be unsubstituted, monosubstituted or disubstituted, in which case the substituents may be selected in turn from the group $\alpha$;

or two adjacent residues $R_7$ form a fused-on benzene ring, which may be unsubstituted, monosubstituted or disubstituted, in which case the substituents may be selected in turn from the group $\alpha$;

and B and B' are each independently selected from one of the following groups a) or b), where a) are mono-, di- and trisubstituted aryl residues, where the aryl residue is phenyl, naphthyl or phenanthryl;

b) are unsubstituted, mono- and disubstituted heteroaryl residues, where the heteroaryl residue is pyridyl, furanyl, benzofuranyl, thienyl, benzothienyl, 1,2,3,4-tetrahydrocarbazolyl or julolidinyl, where the substituents of the aryl or heteroaryl residues in a) and b) are those selected from the previously defined group $\alpha$ or the group $\chi$, consisting of amino, mono-($C_1$-$C_6$)-alkylamino, di-($C_1$-$C_6$)-alkylamino, mono- and diphenylamino unsubstituted, mono- or disubstituted on the phenyl ring, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, unsubstituted, mono- or disubstituted phenothiazinyl, unsubstituted, mono- or disubstituted phenoxazinyl, unsubstituted, mono- or disubstituted 1,2,3,4-tetrahydroquinolinyl, unsubstituted, mono- or disubstituted 2,3-dihydro-1,4-benzoxazinyl, unsubstituted, mono- or disubstituted 1,2,3,4-tetrahydroisoquinolinyl, unsubstituted, mono- or disubstituted phenazinyl, unsubstituted, mono- or disubstituted carbazolyl, unsubstituted, mono- or disubstituted 1,2,3,4-tetrahydrocarbazolyl and unsubstituted, mono- or disubstituted 10,11-dihydrodibenz[b,f]azepinyl, where the substituents in turn may each independently be selected from ($C_1$-$C_6$)-alkyl, ($C_1$-$C_6$)-alkoxy, bromine, chlorine or fluorine;

or where two directly adjacent substituents of the aryl or heteroaryl residues in a) and b) are a V—($CR_8R_9$)$_p$—W moiety, where p=1, 2 or 3, the residues $R_8$ and $R_9$ are each independently a substituent selected from the group $\alpha$, and where V and W may each independently be —O—, —S—, —N($C_1$-$C_6$)alkyl, —N$C_6H_5$, —$CH_2$—, —C($CH_3$)$_2$— or —C($C_6H_5$)$_2$—, where two or more adjacent $CR_8R_9$ units of this V—($CR_8R_9$)$_p$—W moiety may be part of a benzene ring fused thereto, which in turn may each have one or more substituents selected from the group $\alpha$, or V and/or W together with the respective adjacent $CR_8R_9$ unit is a fused benzene ring, which may be unsubstituted, mono- or disubstituted, of which the substituents may be selected from the group $\alpha$.

The compounds according to the invention, compared to the photochromic 2H-naphtho[1,2-b]pyrans known in the prior art (U.S. Pat. No. 5,645,767), which do not have a second indeno fusion, are characterized in that they exhibit a double absorption band, i.e. two bands, of the open form in the visible wavelength range, if a second indeno fusion is introduced. The first of the two strong absorption bands has an absorption maximum of >500 nm while the maximum of the second band lies in the shorter wavelength visible range (400-500 nm). Owing to the latter band, it is possible with the compounds according to the invention to dispense with yellow- or orange-darkening photochromic dyes in neutral-color phototropic glasses. This is important on the one hand for polymer systems in which these yellow- and orange-darkening dyes—owing to their different molecular structure compared to the longwave absorbing violet- and blue-darkening dyes—have an insufficient lifetime or are accompanied by other disadvantages. On the other hand it is possible for the first time with the photochromic dyes according to the invention, in neutral colors—i.e. in grey or brown hues—to achieve darkening phototropic glasses with only one photochromic dye. The cumbersome balancing process between the different photochromic dyes of a mixture with respect to rate of lightening, lifetime and spectral excitation properties required to date is thus eliminated, so that the phototropic glass has the same hue at each time point of the darkening and lightening cycle.

Moreover, since the compounds according to the invention have a high clarity (i.e. high transmission in the non-excited state) and very good light stability, they are eminently suitable for use in phototropic glasses.

In one embodiment of the present invention, the residues $R_1$ and $R_2$ are each independently selected from a hydrogen atom, a ($C_1$-$C_6$)-alkyl residue or a ($C_3$-$C_7$)-cycloalkyl residue, preferably from a ($C_1$-$C_6$)-alkyl residue or a ($C_3$-$C_7$)-cycloalkyl residue.

In another embodiment of the present invention, the residues $R_1$ and $R_2$, together with the carbon atom bonded to these residues, form a 5- to 7-membered carbocyclic or heterocyclic ring, which optionally carries one or more substituents from the group α.

In a further embodiment of the present invention, the residues $R_5$ and $R_6$ are each independently selected from a hydrogen atom, a ($C_1$-$C_6$)-alkyl residue or a ($C_3$-$C_7$)-cycloalkyl residue, preferably from a ($C_1$-$C_6$)-alkyl residue.

Preferred photochromic double-indeno-fused naphthopyrans in accordance with the present invention have the following general formula (II):

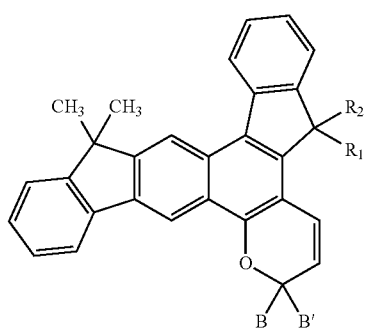
(II)

where the residues $R_1$, $R_2$, B and B' are as defined above.

In a further preferred embodiment, the residues B and B' are each independently selected from the group a), as defined above.

The substituents of the group χ which have nitrogen atoms or bear amino groups are attached via the latter to the phenyl, naphthyl or phenanthryl residue of the group a).

With regard to the substituents of the group V—($CR_8R_9$)$_p$—W moiety which may be attached to the phenyl, naphthyl or phenanthryl residue of group a) for the B or B' residues, when two or more adjacent carbon atoms of this V—($CR_8R_9$)$_p$—W moiety are each independently part of a benzo ring system fused thereto, this means that the two methylene carbon atoms (—$CH_2$—$CH_2$—) then become part of a fused ring system. When, for example, two or three benzo rings are fused, it is possible, for example, for the following structural units as shown below to be present:

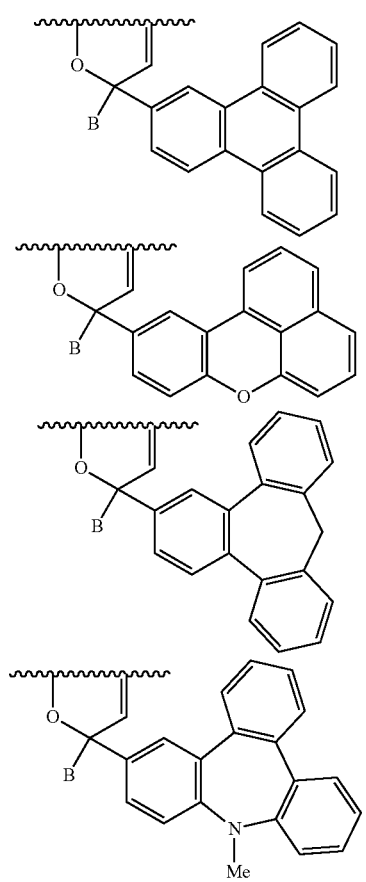

It will be appreciated, however, that it is also possible for only one benzo ring fused via two adjacent carbon atoms of this V—($CR_8R_9$)$_p$—W moiety to be present.

As already explained, the compounds according to the invention, compared to the photochromic 2H-naphtho[1,2-b]pyrans known in the prior art (U.S. Pat. No. 5,645,767), which do not have a second indeno fusion, surprisingly have a second strong absorption band of the open form in the visible wavelength range (see FIG. 2). The formation of this second absorption band in the compounds according to the invention is, in this respect, unexpected.

To measure the spectral properties of the compounds according to the invention, 350 ppm of each photochromic dye were dissolved in acrylate monomer matrix and, following addition of a polymerization initiator, were thermally polymerized with the aid of a temperature programme. The transmission properties in the excited state of the plastic lenses thus produced (thickness 2 mm) were subsequently analyzed according to DIN EN ISO 8980-3.

Figure 2:
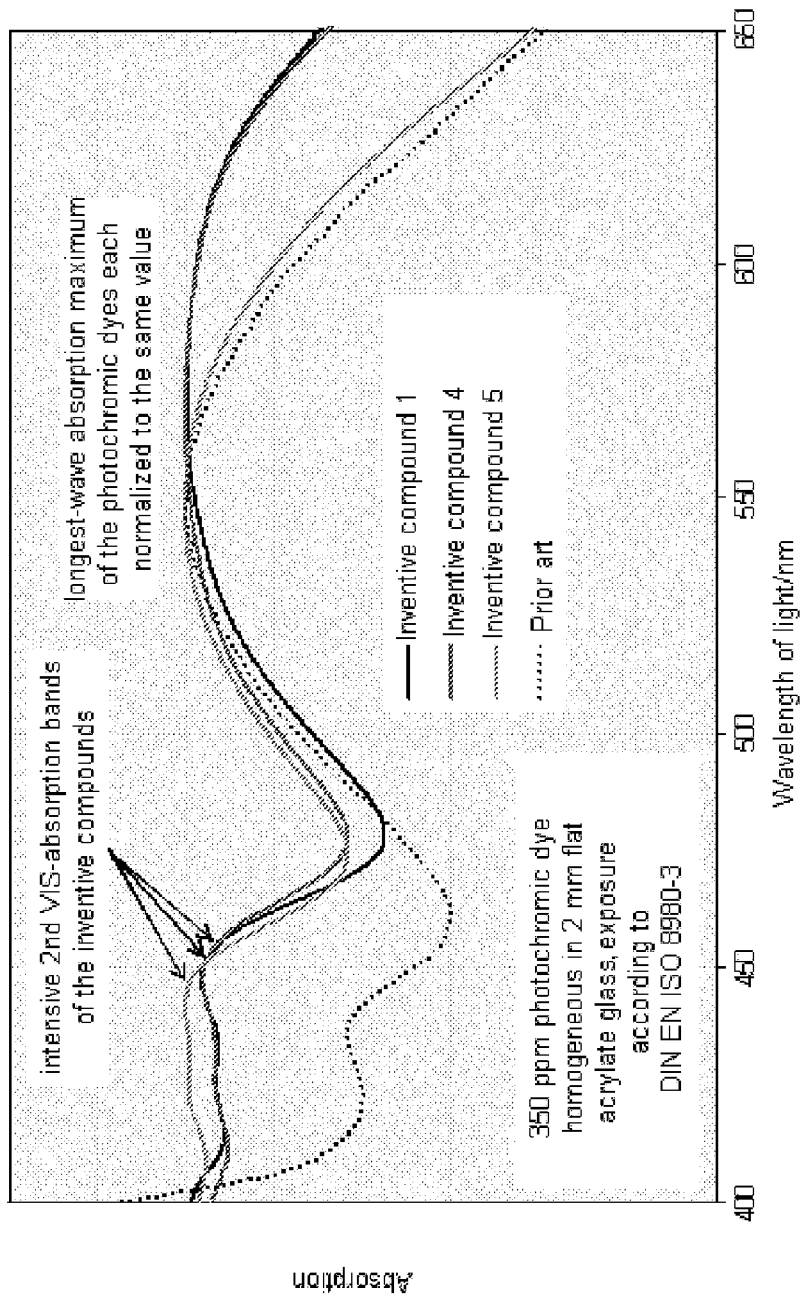
FIG. 2 shows the UV absorption spectra of specific compounds according to the invention in comparison with the prior art.

The structures of the compounds used or investigated in FIG. 2 are shown in the table below:

TABLE 1

Tabular comparison of the longest-wave absorption maximum in the excited state (An = anisyl, i.e. the 4-methoxyphenyl residue)

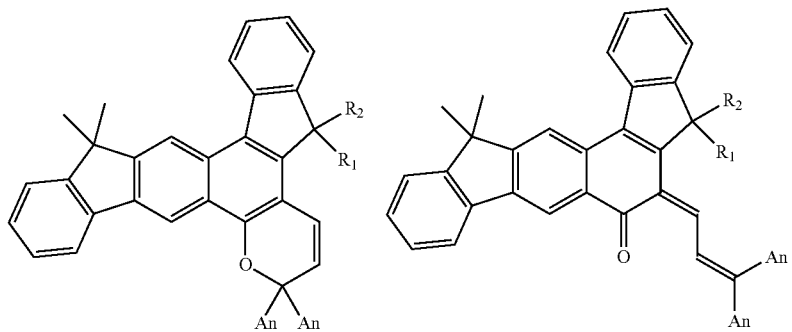

| | | | λmax | λmax | Colour |
| | R₁ | R₂ | (1) | (2) | impression |
| --- | --- | --- | --- | --- | --- |
| Prior art from U.S. Pat. No. 5,645,767 (without the inventive second fused indeno ring) | methyl | methyl | — | 550 nm | violet |
| Inventive compound 1 | methyl | methyl | 450 nm | 575 nm | blue-greenish grey |
| Inventive compound 2 | ethyl | ethyl | 450 nm | 575 nm | blue-greenish grey |
| Inventive compound 3 | propyl | propyl | 450 nm | 575 nm | blue-greenish grey |
| Inventive compound 4 | —(CH₂)₅— (spiro ring) | | 450 nm | 575 nm | blueish grey |
| Inventive compound 5 | cyclohexyl | cyclohexyl | 440 nm | 550 nm | red violet |

FIG. 2 shows the UV absorption spectra of the inventive compounds 1, 4 and 5 in comparison to the prior art. The formation of a double absorption band in the case of the inventive compound 1, in contrast to the prior art, clearly shows the influence of the second indeno fusion on the absorption spectrum—for the otherwise identical molecular structure (see FIG. 2). The inventive compounds 2 and 3 have absorption characteristics identical with those of compound 1.

The hypsochromic shift of the two absorption bands for inventive compound 5, in comparison to the other inventive compounds, is striking. Furthermore, even in the case of the quantitative measurement of the depth of darkening, this compound exhibits a much lower saturation absorption (see table 2). Since the compound is pure according to HPLC/NMR, the differences observed relative to the other inventive compounds can be explained only by the greater steric load resulting from the two very bulky cyclohexyl substituents. As a result, the upper benzene ring is rotated out of the molecular plane, and its conjugation with the rest of the molecule is hindered. This then leads to the observed hypsochromic shift of the absorption bands, and reduction in the attainable depth of darkening.

Table 2 shows an overview of the depth of darkening in the excited state and also the lightening rate of the inventive compounds (formulae analogous to table 1; measurement on polymeric glass plates 2 mm thick in accordance with DIN EN ISO 8980-3, in each case at 23° C.).

TABLE 2

Photochromic properties of the inventive compounds

| Inventive compound | 4 | 1 | 2 | 3 | 5 |
| --- | --- | --- | --- | --- | --- |
| Saturation absorption at 23° C. (excited state) | 95% | 90% | 88% | 85% | 78% |
| Lightening attained after 2 minutes at 23° C. * | 4 rel % | 17 rel % | 28 rel % | 27 rel % | 15 rel % |
| Lightening attained after 10 minutes at 23° C. * | 25 rel % | 59 rel % | 71 rel % | 69 rel % | 52 rel % |

* stated in relation to the initial state: 100 rel % would denote complete lightening relative to the initial state (the higher the figure, the faster the lightening rate)

The inventive compounds are indicated in table 2 from left to right in accordance with increasing size of the substituents $R_1$ and $R_2$. The inventive compound 4 exhibits the smallest steric load resulting from $R_1$ and $R_2$ (both together form a six-membered spiro ring), and the greatest observed saturation absorption (depth of darkening). The lightening rate, however, is by far the slowest in the series. The inventive compound 5 has the greatest steric load resulting from $R_1$ and $R_2$ (two very bulky cyclohexyl residues).

Normally it would be expected that the lightening rate at a constant temperature, owing to the photochromatic reaction mechanism (molecular opening into the excited form through UV light; thermal reaction back into the non-excited form), is indirectly proportional to the saturation absorption—in other words, the deeper the darkening of a photochromic compound, the slower it normally lightens. Interestingly, however, in the series in table 2, a maximum is apparent in the lightening rate. The reason for this lies in the aforementioned strong steric load of the inventive compound 5 (and, though less so, of compound 3 as well), which results in a twisting of the molecule and, accompanying this twisting, a lower saturation absorption.

The inventive compound 2 exhibits not only a decidedly deep saturation absorption but also a decidedly rapid lightening rate.

Table 2 shows that the photochromic properties can be tailored through the selection of the substituents $R_1$ and $R_2$. All of the compounds, however, have the desired double absorption character in the excited form.

Through the present invention, a class of new photochromic double absorption dyes is provided, which includes not only compounds with extremely deep darkening and a slow lightening rate (for photochromic outdoor products and relatively high temperatures), and compounds with a faster lightening rate (for photochromic everyday glasses).

Figure 1:
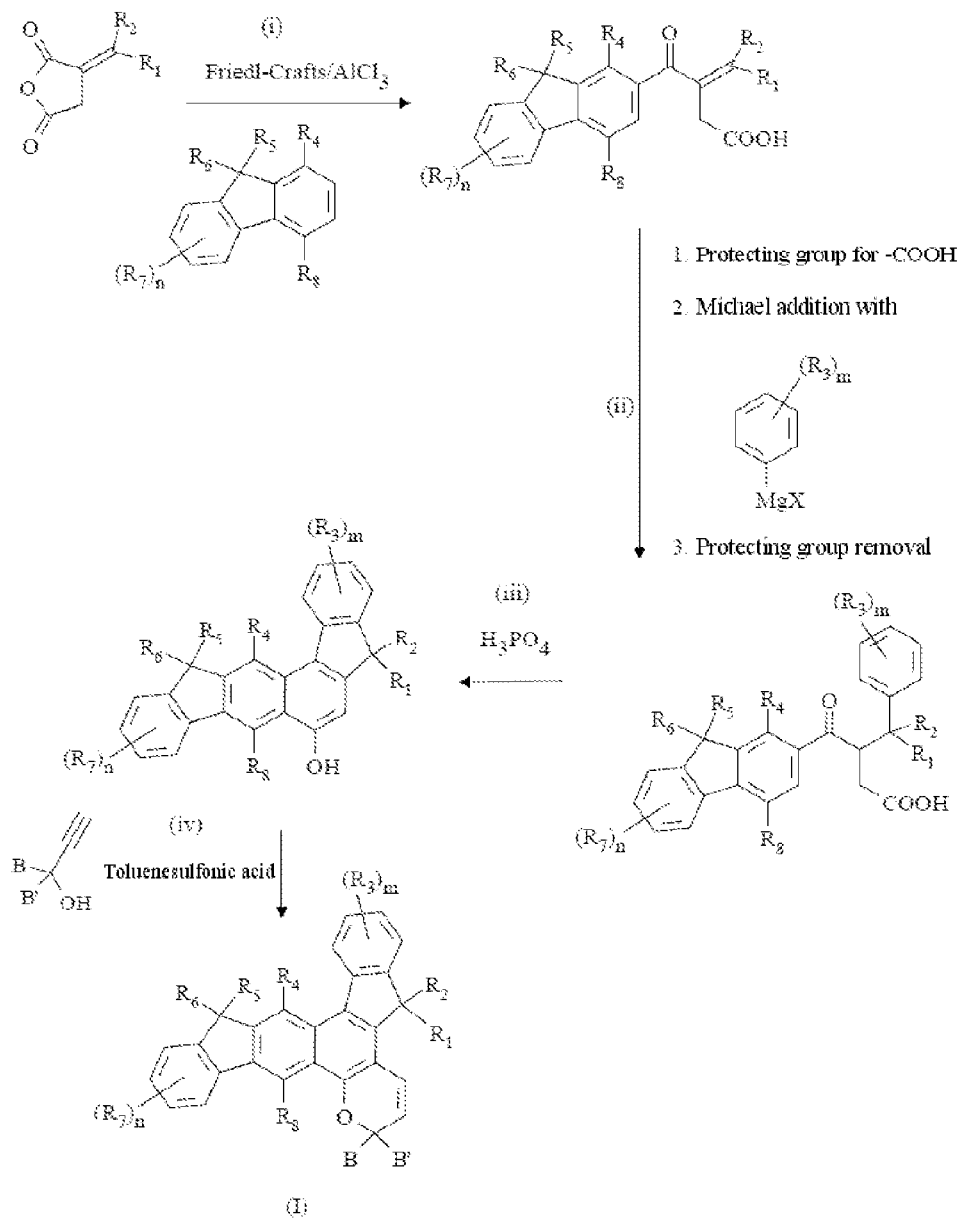
FIG. 1 shows a corresponding synthetic scheme for preparing the compounds according to the invention.

To synthesize the compounds according to the invention, suitably substituted methylidenesuccinic anhydrides are subjected in a first step to a Friedel-Crafts reaction with suitably substituted fluorene derivatives (step (i)). The COOH group of the resulting intermediate is subsequently protected and this intermediate is subjected to a Michael addition with appropriately substituted aryl Grignard compounds (step (ii)). After removal of the carboxylic acid protecting group, correspondingly substituted derivatives are formed via intramolecular cyclization using phosphoric acid (step (iii)). These substituted derivatives are then reacted with suitably substituted 2-propyn-1-ol derivatives to the inventive compounds according to step (iv). The abovementioned synthetic scheme is depicted in FIG. 1.

The compounds according to the invention may be used in plastic materials or plastic items of every type and form for a variety of purposes for which photochromic behavior is of interest. Here, a dye according to the present invention or a mixture of such dyes may be used. For example, the photochromic double-indeno-fused naphthopyrans dyes according to the invention may be used in lenses, particularly ophthalmic lenses, lenses for spectacles of all types, such as ski goggles, sunglasses, motorcycle goggles, visors of helmets and the like. Furthermore, the photochromic double-indeno-fused naphthopyrans dyes according to the invention can also be used, for example, as sun protection in vehicles and homes in the form of windows, protective screens, covers, roofs and the like.

For the preparation of such photochromic items, the photochromic double-indeno-fused naphthopyrans according to the invention can be applied to, or embedded in, a polymeric material, such as an organic plastic material, by various methods described in the prior art, such as already indicated in WO 99/15518.

We distinguish here between so-called mass coloring and surface staining procedures. A mass coloring procedure comprises, for example, the dissolving or dispersing of the photochromic compound or compounds according to the present invention in a plastic material, for example, by the addition of the photochromic compound(s) to a monomeric material before the polymerisation is carried out. A further possibility for producing a photochromic article is to permeate the plastic material(s) with the photochromic compound(s) by immersing the plastic material in a hot solution of the photochromic dye(s) according to the present invention or, for example, by a thermal transfer process. The photochromic compound(s) may also be provided, for example, in the form of a separate layer between adjacent layers of plastic material, for example, as part of a polymeric film. Further, it is also possible to deposit the photochromic compound(s) as part of a layer present on the surface of the plastic material. The term "permeation" here is intended to mean the migration of the photochromic compound(s) into the plastic material, for example, by the solvent-assisted transfer of the photochromic compound(s) in a polymer matrix, vapor phase transfer or other such surface diffusion processes. Advantageously, such photochromic articles, such as lenses, can be produced not only by means of conventional mass coloring, but also in the same manner by means of surface staining, where in the latter variant a surprisingly low migration tendency can be achieved. This is a particular advantage in the subsequent processing steps, since—for example, as with an antireflective coating due to the lower back diffusion in a vacuum—delamination and similar defects are drastically reduced.

Overall, based on the photochromic double-indeno-fused naphthopyrans according to the invention, any compatible (in chemical terms and in a color-dependent manner) stains, i.e. dyes, may be applied to, or embedded in, the plastic material in order to satisfy both aesthetic aspects and medical or fashion aspects. The specifically selected dye(s) may therefore vary, depending on the intended effects and requirements.

The invention claimed is:

1. Photochromic double-indeno-fused naphthopyrans having the general formula (I):

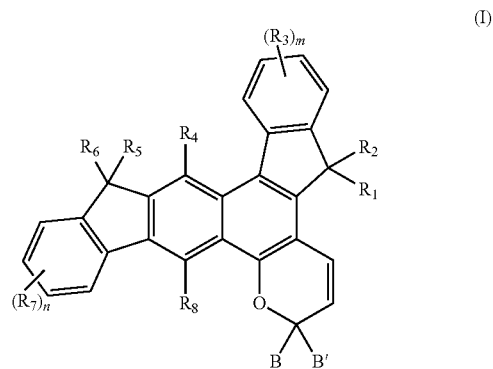

where the residues $R_1$, $R_2$, $R_3$, $R_4$, $R_5$, $R_6$, $R_7$ and $R_8$ are each independently a substituent selected from the group α, consisting of a hydrogen atom, a $(C_1-C_6)$-alkyl residue, a $(C_1-C_6)$-thioalkyl residue, a $(C_3-C_7)$-cycloalkyl residue, which may have one or more heteroatoms, a $(C_1-C_6)$-alkoxy residue, a hydroxyl group, a trifluoromethyl group, bromine, chlorine, fluorine, an unsubstituted, monosubstituted or disubstituted phenyl, phenoxy, benzyl, benzyloxy, naphthyl or naphthoxy residue, in which the substituents may in turn be selected from the group α, preferably from $(C_1$-$C_6)$-alkyl, $(C_1C_6)$-akloxy, bromine, chlorine or fluorine; m and n are each independently an integer from 1 to 4, or the residues $R_1$ and $R_2$, together with the carbon atom bonded to these residues, form a 5- to 7-membered carbocyclic or heterocyclic ring, which optionally carries one or more substituents from the group α, it also being possible, however, for one to three aromatic or heteroaromatic ring systems to be fused onto this ring, the ring system or ring systems being selected independently of one another from the group β, consisting of benzene, naphthalene, phenanthrene, pyridine, quinoline, furan, thiophene, pyrrol, benzofuran, benzothiophene, indol and carbazol, which may in turn be substituted by one or more substituents selected from the group α, and where, if two of these substituents borne by the 5- to 7-membered carbocyclic or heterocyclic ring are located on the same ring carbon atom, they may in turn form a 5- to 7-membered carbocyclic or heterocyclic ring, or the residues $R_5$ and $R_6$, together with the carbon atom bonded to these residues, form a 5- to 7-membered carbocyclic or heterocyclic ring, which optionally carries one or more substituents from the group α, it also being possible, however, for one to three aromatic or heteroaromatic ring systems to be fused onto this ring, the ring system or ring systems being selected independently of one another from the group β, consisting of benzene, naphthalene, phenanthrene, pyridine, quinoline, furan, thiophene, pyrrol, benzofuran, benzothiophene, indol and carbazol, which may in turn be substituted by one or more substituents selected from the group α, and where, if two of these substituents borne by the 5- to 7-membered carbocyclic or heterocyclic ring are located on the same ring carbon atom, they may in turn form a 5- to 7-membered carbocyclic or heterocyclic ring, or two adjacent residues $R_3$ form a fused-on benzene ring, which may be unsubstituted, monosubstituted or disubstituted, in which case the substituents may be selected in turn from the group α;

or two adjacent residues $R_7$ form a fused-on benzene ring, which may be unsubstituted, monosubstituted or disubstituted, in which case the substituents may be selected in turn from the group α;

and B and B' are each independently selected from one of the following groups a) or b), where
  a) are mono-, di- and trisubstituted aryl residues, where the aryl residue is phenyl, naphthyl or phenanthryl;
  b) are unsubstituted, mono- and disubstituted heteroaryl residues, where the heteroaryl residue is pyridyl, furanyl, benzofuranyl, thienyl, benzothienyl, 1,2,3,4-tetrahydrocarbazolyl or julolidinyl,
where the substituents of the aryl or heteroaryl residues in a) and b) are those selected from the previously defined group α or the group χ, consisting of amino, mono-$(C_1$-$C_6)$-alkylamino, di-$(C_1$-$C_6)$-alkylamino, mono- and diphenylamino unsubstituted, mono- or disubstituted on the phenyl ring, piperidinyl, N-substituted piperazinyl, pyrrolidinyl, imidazolidinyl, pyrazolidinyl, indolinyl, morpholinyl, 2,6-dimethylmorpholinyl, thiomorpholinyl, azacycloheptyl, azacyclooctyl, unsubstituted, mono- or disubstituted phenothiazinyl, unsubstituted, mono- or disubstituted phenoxazinyl, unsubstituted, mono- or disubstituted 1,2,3,4-tetrahydroquinolinyl, unsubstituted, mono- or disubstituted 2,3-dihydro-1,4-benzoxazinyl, unsubstituted, mono- or disubstituted 1,2,3,4-tetrahydroisoquinolinyl, unsubstituted, mono- or disubstituted phenazinyl, unsubstituted, mono- or disubstituted carbazolyl, unsubstituted, mono- or disubstituted 1,2,3,4-tetrahydrocarbazolyl and unsubstituted, mono- or disubstituted 10,11-dihydrodibenz[b,f]azepinyl, where the substituents in turn may each independently be selected from $(C_1$-$C_6)$-alkyl, $(C_1$-$C_6)$-alkoxy, bromine, chlorine or fluorine;

or where two directly adjacent substituents of the aryl or heteroaryl residues in a) and b) are a V—$(CR_8R_9)_p$—W moiety, where p=1, 2 or 3, the residues $R_8$ and $R_9$ are each independently a substituent selected from the group α, and where V and W may each independently be —O—, —S—, —N$(C_1$-$C_6)$alkyl, —N$C_6H_5$, —$CH_2$—, —C$(CH_3)_2$— or —C$(C_6H_5)_2$—, where two or more adjacent $CR_8R_9$ units of this V—$(CR_8R_9)_p$—W moiety may be part of a benzene ring fused thereto, which in turn may each have one or more substituents selected from the group α, or V and/or W together with the respective adjacent $CR_8R_9$ unit is a fused benzene ring, which may be unsubstituted, mono- or disubstituted, of which the substituents may be selected from the group α.

2. The photochromic double-indeno-fused naphthopyrans as claimed in claim 1, where the residues $R_1$ and $R_2$ are each independently selected from a hydrogen atom, a $(C_1$-$C_6)$-alkyl residue or a $(C_3$-$C_7)$-cycloalkyl residue, preferably from a $(C_1$-$C_6)$-alkyl residue or a $(C_3$-$C_7)$-cycloalkyl residue.

3. The photochromic double-indeno-fused naphthopyrans as claimed in claim 1, where $R_1$ and $R_2$, together with the carbon atom bonded to these residues, form a 5- to 7-membered carbocyclic or heterocyclic ring which optionally carries one or more substituents from the group α.

4. The photochromic double-indeno-fused naphthopyrans as claimed in claim 1, where $R_5$ and $R_6$ are each independently selected from a hydrogen atom, a $(C_1$-$C_6)$-alkyl residue or a $(C_3$-$C_7)$-cycloalkyl residue.

5. The photochromic double-indeno-fused naphthopyrans as claimed in claim 1, which have the following general formula(II):

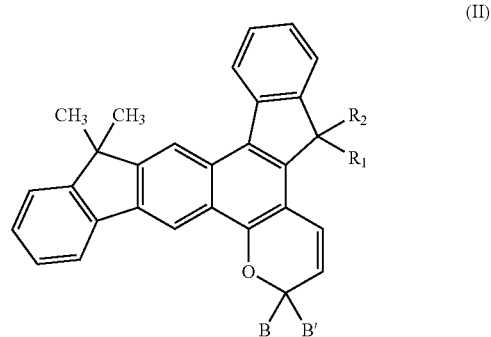

(II)

where the residues $R_1$, $R_2$, B and B' are as defined above.

6. The photochromic double-indeno-fused naphthopyrans as claimed in claim 1, wherein the residues B and B' are each independently selected from the group a), as defined above.

7. A plastic material comprising one or more photochromic naphthopyrans as claimed in claim 1.

8. The plastic material of claim 7, wherein the plastic material is an ophthalmic lens.

* * * * *